(12) United States Patent
Rambach

(10) Patent No.: US 8,728,746 B2
(45) Date of Patent: May 20, 2014

(54) SALMONELLA SELECTIVE ENRICHMENT MEDIUM CONTAINING TETRATHIONATE AND MAGNESIUM SALT

(76) Inventor: Alain Rambach, Paris (FR)

( * ) Notice: Subject to any disclaimer, the term of this patent is extended or adjusted under 35 U.S.C. 154(b) by 281 days.

(21) Appl. No.: 12/781,329

(22) Filed: May 17, 2010

(65) Prior Publication Data

US 2010/0227360 A1   Sep. 9, 2010

Related U.S. Application Data

(62) Division of application No. 11/572,746, filed as application No. PCT/FR2005/001724 on Jul. 5, 2005, now abandoned.

(30) Foreign Application Priority Data

Jul. 27, 2004 (FR) .................................. 04 08276

(51) Int. Cl.
*G01N 33/554* (2006.01)

(52) U.S. Cl.
USPC ...................................... 435/7.32; 435/7.35

(58) Field of Classification Search
USPC ............................... 435/7.32, 7.35
See application file for complete search history.

(56) References Cited

FOREIGN PATENT DOCUMENTS

| EP | 1 253 203 | 10/2002 |
|---|---|---|
| WO | WO 96/00794 | 1/1996 |
| WO | WO 94/28163 | 12/2004 |

OTHER PUBLICATIONS

Beckers et al. "Evaluation of reference samples for the detection of Salmonella", International J of Food Microbiology, 1986, 3:287-298.*
ISO 6579: 2002. International standard: Microbiology of food and animal feeding stuffs—Horizontal method for the detection of Salmonells spp. p. i-27.*
Blivet et al., *Evaluation of a New Enrichment Broth for the Isolation of Salmonella spp. From poultry Products*, International Journal of Food Microbiology, vol. 38 Elsevier Science B.V., (1997), pp. 211-216.
Harvey et al., *Comparison of Selenite F, Muller-Kauffmann Tetrathionate and Rappaport's Medium for Salmonella Isolation From Chicked Giblets After Pre-Enrinchment in Buffered Peptone Water*, J. Hyg. Camb., 87, (1981), pp. 219-224.
Idachaba et al., *Evaluation of Microbial Stability of Simulated Solid and Liquid Waste Forms Using a Refined Biofilm Formation Method*, Journal of Hazardous Materials, B90, (2002), pp. 279-295.
Lindstrom et al., *High Efficiency of Plating of the Thermophilic Sulfur-Dependent Archaebacterium Sulfolobus Acidocaldarius*, Applied and Environmental Microbiology, 55(11), (1989), pp. 3020-3021.
Nishihara et al., *Growth Characteristics and High Cell-Density Cultivation of a Marine Obligately Chemolithoautotrophic Hydrogen-Oxidizing Bacterium Hydrogenovibrio marinus Strain MH-110 Under a Continuous Gas-Flow System*, Journal of Fermentation and Bioengineering, vol. 72, No. 5, (1991), pp. 358-361.
Szita et al., *A Novel, Selective Synthetic Acetamide Containing Culture Medium for Isolating Pseudomonas aeruginosa From Milk*, International Journal of Food Microbiology, 43, (1998), pp. 123-127.

* cited by examiner

*Primary Examiner* — Bin Shen
(74) *Attorney, Agent, or Firm* — Alston & Bird LLP

(57) ABSTRACT

The invention relates to a salmonella selective enrichment medium containing tetrathionate or a salt thereof and at least one type of magnesium salt and to a method for detecting salmonella in a sample by using said selective enrichment medium.

8 Claims, No Drawings

SALMONELLA SELECTIVE ENRICHMENT MEDIUM CONTAINING TETRATHIONATE AND MAGNESIUM SALT

CROSS-REFERENCE TO RELATED APPLICATIONS

This application is a divisional of U.S. application Ser. No. 11/572,746 (now abandoned), filed Jan. 26, 2007, which was a national stage filing under 35 U.S.C. 371 of PCT/FR2005/001724 filed Jul. 5, 2005, which claims priority to French Application No. 0408276, filed Jul. 27, 2004, each of which is incorporated herein by reference in their entirety.

The present invention relates to a salmonella selective enrichment medium containing tetrathionate or a salt thereof and at least one magnesium salt, as well as a method for detecting salmonella in a sample by using said selective enrichment medium.

Salmonella are at the origin of animal diseases that can be transmitted to man, notably through the food supply, and whose development can cause pathogenic effects. They have long been recognized as sources of foodborne illnesses. Their detection is thus very important, in particular with respect to water monitoring in the food industry, as well as in the field of medicine. Various methods are capable of detecting the presence of salmonella in a suspect sample. Some of these methods include a step of growing the possibly present salmonella by placing said sample in contact with a salmonella specific enrichment medium.

Liquid, semi-solid or solid enrichment media inoculated with a polymicrobial product that contains salmonella make it possible to increase the growth and proportion of salmonella and then to detect them in a sample.

For many years, three enrichment media formula families have been widely used that contain, as a selective agent, either selenite (since 1936), or tetrathionate, optionally made extemporaneously from thiosulfate and an iodo-iodide solution (since 1923), or a high-concentration magnesium salt (since 1956).

However, the salmonella enrichment media available on the market have variable effectiveness depending on various factors such as the strains to detect, the type of sample or the competitive flora found in the samples.

Furthermore, one of the principal areas of technological research and development relates to salmonella detection speed. Thus, the most recent techniques involving "DNA chips" not only make it possible to carry out presence/absence tests but also to quantify the bacteria possibly present. However, such techniques are complex to implement, costly and do not indicate the viability of the bacteria. This leads to additional detection time.

Thus, currently there is a need for a salmonella detection technique that is effective, whose effectiveness does not vary depending on various factors, and that rapidly detects living salmonella.

In a surprising and unexpected way, the inventor has demonstrated that two salmonella selective agents, namely tetrathionate and a magnesium salt, are compatible with each other in such a way that they can be combined to obtain an effective and robust enrichment medium with improved performance compared to conventional selective medium enrichment methods.

In addition, the method described also has the advantage that the total time required to indicate the presence or absence of salmonella in the sample tested can be reduced to a maximum of 44 hours, whereas traditional methods require an initial period of 48 hours (24 hours of culture in a reactivation medium then 24 hours of culture in a selective medium) before an isolation step on a selective medium (18-24 hours), which is a total of 66 to 72 hours.

Thus, the present invention relates to a salmonella selective enrichment medium wherein said medium is comprised of tetrathionate or a salt thereof and at least one magnesium salt.

In the enrichment medium of the invention, the magnesium salt is used at a concentration sufficient to create high osmotic pressure in said medium. Thus, all other compounds having a similar effect on osmotic pressure in an aqueous medium may also be used to replace or to supplement said magnesium salt.

According to a preferred embodiment of the present invention, said magnesium salt is present in the enrichment medium of the invention at a concentration between 0.1 g/l and 50 g/l, preferably between 2 g/l and 40 g/l and more preferentially still between 7 g/l and 35 g/l.

The magnesium salt is preferably selected among magnesium carbonate, magnesium chloride or magnesium sulfate.

According to a preferred embodiment of the present invention, tetrathionate or a salt thereof is present in the enrichment medium of the invention at a concentration between 0.1 g/l and 40 g/l, preferably between 0.5 g/l and 30 g/l and more preferentially still between 1 g/l and 25 g/l.

The tetrathionate salt is preferably selected among potassium tetrathionate and sodium tetrathionate, regardless of the magnesium salt used.

The present invention also relates to a method for detecting salmonella in a sample comprising the following steps:
  salmonella reactivation by incubating said sample in a reactivation broth,
  salmonella enrichment by incubating an aliquot of the reactivation medium in a salmonella selective enrichment medium, and
  salmonella isolation,
wherein the selective enrichment medium used for the enrichment step is such as defined according to the present invention.

The reactivation (or pre-enrichment) step is the step that allows the growth and multiplication of the salmonella, including those in dormancy. This step also makes it possible for stressed bacteria to recover their stability.

Within the framework of the salmonella detection method of the present invention, the duration of this step is considerably reduced (approximately 4 hours according to the invention, compared to approximately 24 hours according to the prior art) because of the quality of the subsequent enrichment step. Indeed, the enrichment medium of the invention makes it possible to enrich salmonella in the reactivation medium in such a way that the reactivation step does not need to be carried out for more than approximately 4 hours in order for it to play its part fully.

It should to be stressed that this reactivation step is in no way obligatory and thus is optional within the framework of the present invention. It is, however, particularly advantageous when the method of the invention is implemented in the food industry because the nature of food safety requires reliable detection of any salmonella possibly present in the sample tested, including salmonella in dormancy.

The salmonella isolation step is carried out in a conventional way well known to those skilled in the art. Considering the high concentration of salmonella obtained in the medium following the enrichment step, this isolation step does not need to be selective (i.e., make it possible to detect salmonella with respect to other bacteria) and can be specific for salmonella alone.

This isolation step can be carried out by immunological methods or PCR, for example, but also by highly specific methods such as those carried out on agar media for salmonella detection (Hektoen agar, etc.).

In a specific embodiment of said method, the isolation step includes an analysis procedure chosen from the group consisting in enzymatic immunological analyses; nucleic acid probe hybridization analyses; pure culture analyses; analyses using biochemical indicators, in particular those developed by colorimetric methods; and immunoimmobilization analyses. The technique can be cited as an example of an isolation analysis.

The method according to the present invention can be used to test food and beverage samples; environmental samples of solids, liquids, such as water, or air; or clinical samples.

The invention is not only limited to the description above and the example below is given only for purposes of illustration.

EXAMPLE

Comparison of a liquid enrichment medium containing tetrathionate alone as a selective factor and a liquid enrichment medium containing tetrathionate and a magnesium salt in accordance with the invention.

Each sample consists of 25 ml of yogurt, in one case inoculated with a mixture of 100 *Salmonella* and 1,000,000 *E. coli* and in another case with 100 *Salmonella* and 1,000,000 *Citrobacter*, so that the salmonella are in a 1:10,000 ratio with respect to the competitive flora.

1. Reactivation

Each sample is mixed with 225 ml of a reactivation broth of formula (In grams per liter of water): peptone, 5; NaCl, 5; calcium carbonate, 10.

The mixture is incubated at 37° C. for 4 hours.

2. Enrichment 10 ml of said mixture are recovered in a container and the following are added:

in the case of the control medium, 0.38 g of a supplement of formula (In grams per liter of water): bile, 8; calcium carbonate, 10; brilliant green, 0.07; tetrathionate, 20; or, in the case of the invention, 0.31 g of a supplement of formula (in grams per liter of water): bile, 8; calcium carbonate, 10; brilliant green, 0.07; tetrathionate, 3; magnesium chloride, 10 (Table 1).

TABLE 1

| In g/l | Bile | Calcium carbonate | Brilliant green | Tetrathionate | Magnesium chloride |
|---|---|---|---|---|---|
| Control medium | 8 | 10 | 0.07 | 20 | — |
| Medium according to the invention | 8 | 10 | 0.07 | 3 | 10 |

Enrichment is carried out by incubation of the medium at 37° C. for 22 hours.

3. Isolation

Approximately 10 μl of the culture obtained in step 2 above are isolated on a differential isolation medium and, after 18-24 hours of incubation at 37° C., the *Salmonella* flora and the competitive flora are counted (Table 2).

TABLE 2

| | Proportion of *Salmonella*/competitive flora | |
|---|---|---|
| | *Salmonella*/*E. Coli* mixture | *Salmonella*/*Citrobacter* mixture |
| Control medium | 85% | 1% |
| Medium according to the invention | 100% | 80% |

The invention claimed is:

1. A method for detecting salmonella in a sample, the method comprising:
   reactivating the sample followed by incubating the sample in a salmonella selective enrichment medium comprising (i) from between 1 g/l and 25 g/l of tetrathionate, or a salt thereof, and (ii) from between 7 g/l and 35 g/l of at least one magnesium salt; and
   isolating the salmonella.

2. The method according to claim 1, wherein the reactivating step comprises incubating the sample in a reactivation medium.

3. The method according to claim 1, wherein the isolation step comprises an analysis procedure selected from the group consisting of enzymatic immunological analyses, nucleic acid probe hybridization analyses, pure culture analyses, analyses using biochemical indicators, and immunoimmobilization analyses.

4. The method according to claim 1, wherein the magnesium salt is selected from the group consisting of magnesium carbonate, magnesium chloride, magnesium sulfate, and combinations thereof.

5. The method according to claim 1, wherein the detection of salmonella in the sample is completed in 44 hours or less.

6. The method according to claim 1, wherein the reactivating step is completed in four hours or less.

7. The method according to claim 1, wherein the salmonella selective enrichment medium comprises (i) 3 g/l of tetrathionate, or a salt thereof, and (ii) 10 g/l of at least one magnesium salt.

8. The method according to claim 7, wherein the reactivating step is completed in four hours.

* * * * *